United States Patent
Hung

(10) Patent No.: US 9,005,410 B2
(45) Date of Patent: Apr. 14, 2015

(54) CONTINUOUS ELECTROLYZED OXIDIZING/REDUCTION WATER GENERATOR DEVICE

(76) Inventor: Yun-Chi Hung, Tainan (TW)

( * ) Notice: Subject to any disclaimer, the term of this patent is extended or adjusted under 35 U.S.C. 154(b) by 210 days.

(21) Appl. No.: 13/590,312

(22) Filed: Aug. 21, 2012

(65) Prior Publication Data

US 2013/0048491 A1 Feb. 28, 2013

(30) Foreign Application Priority Data

Aug. 25, 2011 (CN) .......... 2011 1 0246164

(51) Int. Cl.
*C02F 1/461* (2006.01)
*C25B 9/08* (2006.01)

(52) U.S. Cl.
CPC .......... *C02F 1/46104* (2013.01); *C02F 1/4618* (2013.01); *C02F 2001/46142* (2013.01); *C02F 2001/46195* (2013.01); *C02F 2209/04* (2013.01); *C02F 2303/02* (2013.01); *C02F 2303/04* (2013.01)

(58) Field of Classification Search
None
See application file for complete search history.

(56) References Cited

U.S. PATENT DOCUMENTS

| | | | | |
|---|---|---|---|---|
| 4,297,194 A * | 10/1981 | Dotson et al. | ........ | 204/257 |
| 5,427,667 A * | 6/1995 | Bakhir et al. | ........ | 204/260 |
| 5,556,523 A * | 9/1996 | Satoh et al. | ........ | 204/272 |
| 5,676,760 A * | 10/1997 | Aoki et al. | ........ | 134/1.3 |
| 5,858,202 A * | 1/1999 | Nakamura | ........ | 205/746 |
| 5,865,966 A * | 2/1999 | Watanabe et al. | ........ | 204/278.5 |
| 5,965,009 A * | 10/1999 | Shimamune et al. | ........ | 205/742 |
| 6,689,271 B2 * | 2/2004 | Morkovsky et al. | ........ | 205/757 |
| 7,238,272 B2 * | 7/2007 | Sano | ........ | 205/701 |
| 2012/0012466 A1 * | 1/2012 | Sperry et al. | ........ | 205/334 |
| 2012/0228145 A1 * | 9/2012 | Guastella et al. | ........ | 205/337 |

* cited by examiner

Primary Examiner — Harry D Wilkins, III
(74) Attorney, Agent, or Firm — Rosenberg, Klein & Lee

(57) ABSTRACT

A continuous electrolyzed oxidizing/reduction water generator device includes an electrically insulative housing which is an acid, alkali and pressure resistant box with a water inlet and multiple water outlets on opposing sides, positive and negative electrodes are mounted in the electrically insulative housing in parallel and equally spaced by a cation exchange membrane, and an electric control box to provide high voltage DC across the positive and negative electrodes to oxidize intake water into electrolyzed oxidizing/reduction water. Multiple generator units may be connected in series.

6 Claims, 6 Drawing Sheets

CONTINUOUS ELECTROLYZED OXIDIZING/REDUCTION WATER GENERATOR DEVICE

BACKGROUND OF THE INVENTION

1. Field of the Invention

The present invention relates to water treatment technology and more particularly, a continuous electrolyzed oxidizing/reduction water generator device for efficiently electrolyzing water into electrolyzed oxidizing/reduction water.

2. Description of the Related Art

Electrolyzed water or electrolyzed oxidizing water is produced by the electrolysis of ordinary city water containing dissolved sodium chloride. The electrolysis occurs in a specially designed reactor which allows the separation of the cathodic and anodic solutions. In this process, electrolytic reduction water is produced at the cathode side, and electrolytic oxidizing water is produced at the anode side. During electrolysis, a cation exchange membrane is provided between the positive electrode and the negative electrode, allowing ions to pass therethrough and to form an electric current, and prohibiting neutralization of electrolyzed molecules between the cathode and the anode. A reactor of this design is therefore an electrolyzed oxidizing/reduction water generator.

Electrolyzed reduction water contains much hydroxide ions, [OH—] higher then [H+], and much active hydrogen, and has a potential level about −800 mV for providing a reduction effect.

Electrolyzed oxidizing water contains much acid radical ions, [H+] higher then [OH—], and a large amount of oxygen-derived free radicals for providing an oxidizing effect for metical and food applications.

During generation of electrolyzed reduction water, a series of complicated electrochemical reactions are performed, electrolyzed reduction water exhibits significant change in oxidation-reduction potential, acid alkaline level, water particle size, ion composition and existence state and conductivity. Because electrolyzed reduction water contains a large amount of active hydrogen, it can eliminate excessive free radicals in the human body. Experimental researches show effectiveness of electrolyzed reduction water in inhibition of pancreatic cancer and tumor angiogenesis and diabetic nephropathy treatment.

However, conventional electrolyzed oxidizing/reduction water generator devices commonly have the drawbacks of limited electrolytic bath capacity and electrode area, quick deterioration of electrodes, ease of scaling, cleaning difficulty and short service life. Further, commercial electrolyzed oxidizing/reduction water generator devices do not any function for setting and displaying electrolyzed water reduction potential. The electrolyzed water reduction potential can only be passively measured by a measuring instrument. However, the water passage in the measuring instrument may be clogged or partially clogged by impurities or cumulated calcium easily during measurement, leading to a measurement error. Thus, a consumer cannot know accurately whether or not the electrolyzed reduction/oxidizing water meets the standards. Further, most consumers doubt the effectiveness of electrolyzed reduction/oxidizing water in human body.

SUMMARY OF THE INVENTION

The present invention has been accomplished under the circumstances in view. It is therefore the main object of the present invention to provide a continuous electrolyzed oxidizing/reduction water generator device, which is capable of continuously generating electrolyzed oxidizing water.

The technical solution is to arrange positive and negative electrodes inside an acidic and alkali resistance pipeline in a parallel manner. The pipeline and the positive and negative electrodes are configured subject to the desired length that can be as long as several meters. When compared to electrolytic bath designs, the invention greatly increases the electrical discharge area.

In one example of the present invention, the continuous electrolyzed oxidizing/reduction water generator device comprises a positive electrode, a negative electrode, a cation exchange membrane, an electrically insulative housing, and an electric control box. The positive electrode and the negative electrode are arranged inside the electrically insulative housing in a parallel manner along the length of the electrically insulative housing. The electrically insulative housing provides a water inlet at one side thereof for water input, and one or a number of water outlets at an opposite side thereof for water output. The electric control box is electrically connected with the positive and negative electrodes, and adapted to provide a high voltage DV across the positive electrode and the negative electrode for oxidizing intake water into electrolyzed oxidizing water/electrolyzed reduction water.

During preparation of the continuous electrolyzed oxidizing/reduction water generator device, an electrically insulative housing is prepared by acid, alkali and pressure resistant engineering plastics in the form of a box member having a rectangular cross section, defining a water inlet at one side and a plurality of water outlets at an opposite side, A positive electrode and a negative electrode are longitudinally mounted inside the electrically insulative housing in a parallel manner and equally spaced between the two opposite side walls of the electrically insulative housing, further, a cation exchange membrane, is mounted inside the electrically insulative housing in a parallel manner relative to and equally spaced between the positive electrode and the negative electrode. The distance between the positive electrode and the negative electrode is within the range of 2 mm~80 mm, or preferably 50 mm.

Further, during application of the continuous electrolyzed oxidizing/reduction water generator device, block the water outlets and then fill water into the water inlet to fill up the inside space of the continuous electrolyzed oxidizing/reduction water generator device, and then apply 5V~5000V DC, for example, 3000V DC across the positive electrode and the negative electrode for a predetermined length of time. Thereafter, open the three water outlets to discharge water, keeping water intake ratio and the water output ratio in balance. Thus, electrolyzed oxidizing water is being continuously provided. Further, when the positive electrode is electrically conducted, it electrolyzes intake water into electrolyzed oxidizing water having a potential level between 800 mV~1500 mV and an acidic pH value; when the negative electrode is electrically conducted, it electrolyzes intake water into electrolyzed reduction water having a potential level between −800 mV~−1200 mV and an alkaline pH value.

Further, in an alternate form of the present invention, multiple generator units are connected in series with bent tubes to constitute a combination type continuous electrolyzed oxidizing/reduction water generator device in which the positive electrodes and negative electrodes of the multiple generator units are electrically connected, to the electric control box that is adapted to provide a high voltage DC across positive electrodes and negative electrodes of the multiple generator units.

Further, by means of using bent tubes to connect multiple generator units in series, the water passageway defined in the series of generator units can be as long as several meters or longer. When compared to conventional electrolytic bath designs electrolyzed oxidizing/reduction water generators, the invention greatly increases the total discharging electrode surface area the electrical discharge area. Increasing the electrical discharge area relatively increases the water electrolyzing capacity. Thus, the combination type continuous electrolyzed oxidizing/reduction water generator device can electrolyze intake water into electrolyzed oxidizing water/electrolyzed reduction water rapidly and efficiently.

Further, the cation exchange membrane is mounted inside the electrically insulative housing in a parallel manner relative to and equally spaced between the positive electrode and the negative electrode to let positively charged ions pass therethrough, balancing the charges between charges between the anode and the cathode. The use of the cation exchange membrane is an option. If both acidic electrolyzed oxidizing water and alkaline electrolyzed oxidizing water are desired, the cation exchange membrane must be mounted inside the electrically insulative housing between the positive electrode and the negative electrode.

Further, the positive electrode can be a graphite plate, platinum plated metal, ruthenium iridium coated titanium plate, or titanium plate.

Further, potassium chloride, sodium chloride or hydrochloric acid may be added to intake water to obtain hypochlorite in the electrolyzed oxidizing water, improving water disinfection capabilities.

When compared to conventional designs, the invention enables the surface area of the electrodes to be greatly extended as desired, increasing the water electrolyzing capacity to continuously supply electrolyzed oxidizing water. The current density of unit electrode area of the continuous electrolyzed oxidizing/reduction water generator device in accordance with the present invention is much lower than conventional electrolytic bath type designs. Further, the positive electrode material for the continuous electrolyzed oxidizing/reduction water generator device in accordance with the present invention is less corrosive. The invention can simultaneously sterilize the intake water, remove bad smell from the intake water, and decompose hazardous TVOCs, purifying the intake water. Because the intake water keeps flowing in the continuous electrolyzed oxidizing/reduction water generator device, the inside wall of the housing will not scale, avoiding a complicated cleaning work and prolonging the device lifespan. The continuous electrolyzed oxidizing/reduction water generator device can be used in different places for drinking, cleaning, irrigation and industrial water applications.

In generally, the invention can supply electrolyzed oxidizing water continuously for civil and industrial applications.

DETAILED DESCRIPTION OF THE PREFERRED EMBODIMENT

Figure 1:
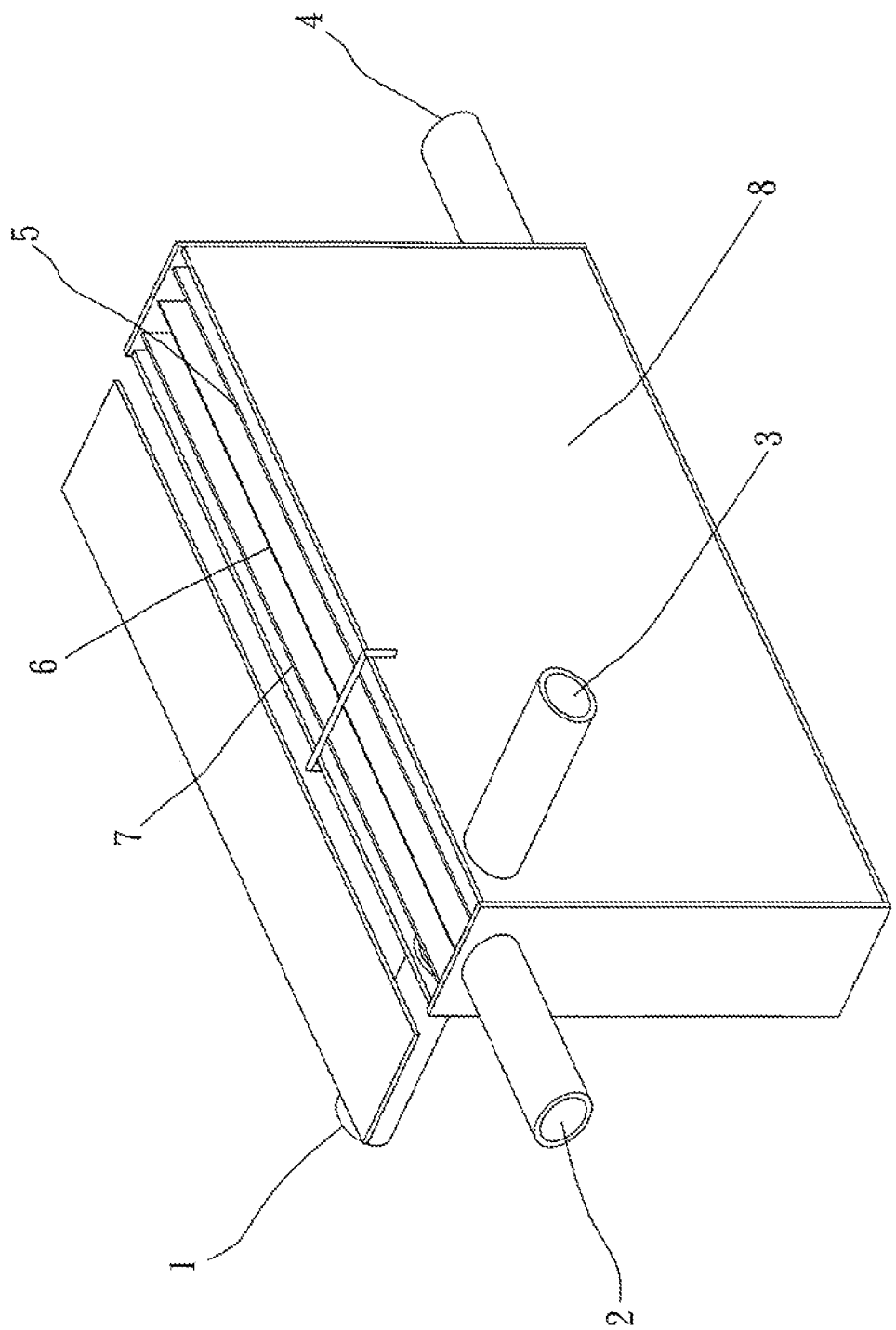
FIG. 1 is an oblique top elevations view of a continuous electrolyzed oxidizing/reduction water generator device in an opened status in accordance with a first embodiment of the present invention.
Figure 2:
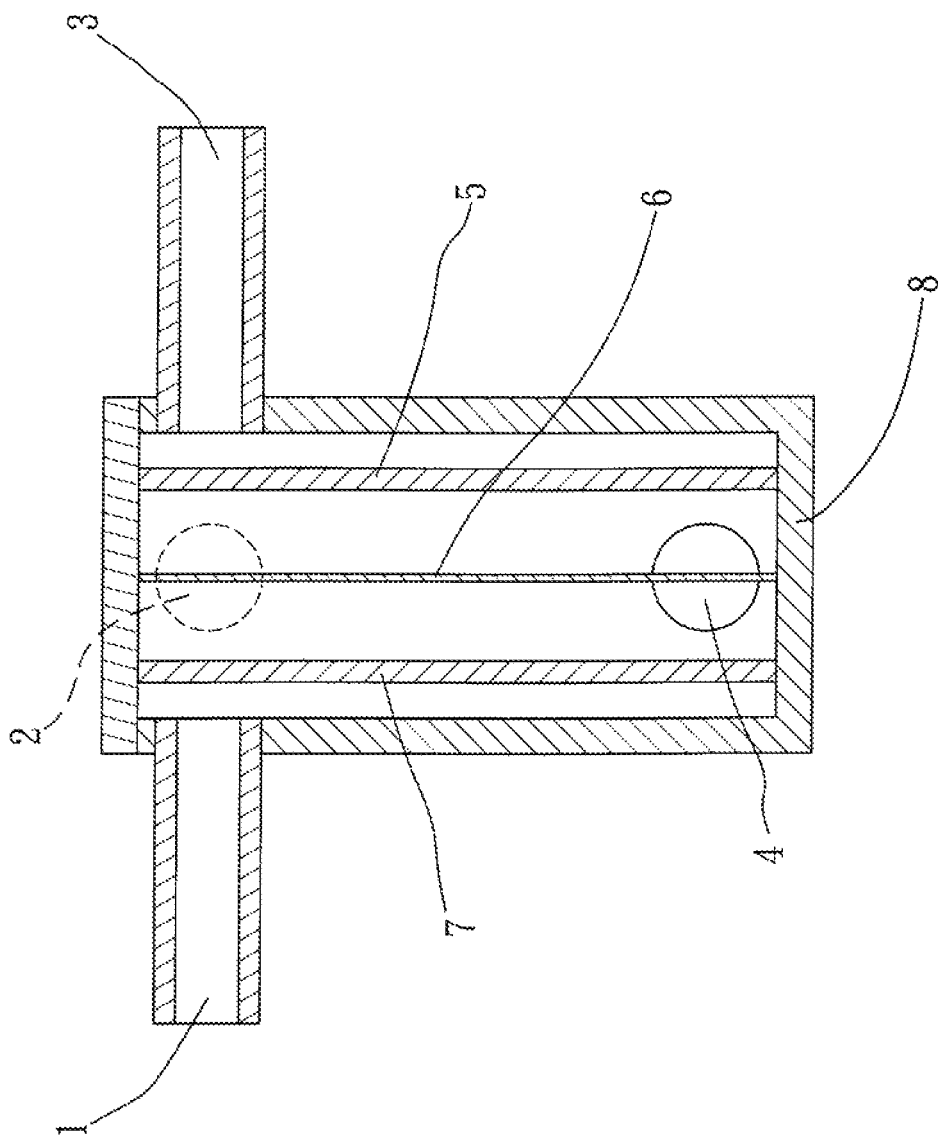
FIG. 2 is a sectional view of the continuous electrolyzed oxidizing/reduction water generator device in accordance with the first embodiment of the present invention.
Figure 3:
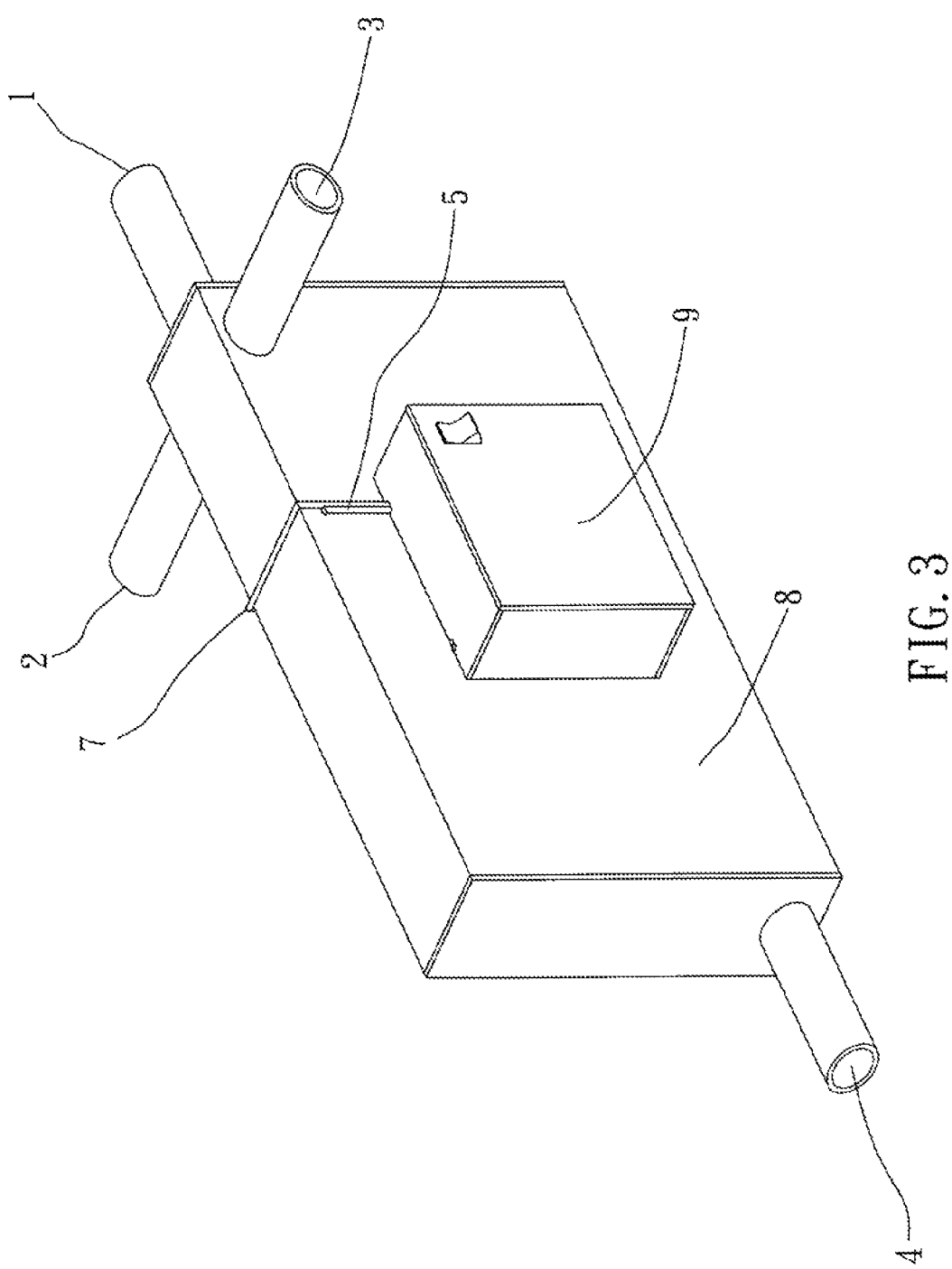
FIG. 3 is another oblique top elevational view of the continuous electrolyzed oxidizing/reduction water generator device in accordance with the first embodiment of the present invention, illustrating the arrangement of the electric control box at the housing.

Referring to FIGS. 1, 2 and 3, a continuous electrolyzed oxidizing/reduction water generator device in accordance with a first embodiment of the present invention is shown. The continuous electrolyzed oxidizing/reduction water generator device comprises a positive electrode 7, a negative electrode 5, a cation exchange membrane 6 an electrically insulative housing 8, and an electric control box 9.

The electrically insulative housing 8 is a box member having a rectangular cross section and made of acid, alkali and pressure resistant engineering plastics, defining a water inlet 4 at one side and three water outlets 1;2;3 at an opposite side. The top panel of the electrically insulative housing 8 is detachable, however, it must be strictly sealed during application. The positive electrode 7 and the negative electrode 5 are longitudinally mounted inside the electrically insulative housing 8 in a parallel manner and equally spaced between the two opposite sidewalk of the electrically insulative housing 8. The positive electrode 7 and the negative electrode 5 are respectively spaced from the two opposite sidewalls of the electrically insulative housing 8 at 5 mm. The distance between the positive electrode 7 and the negative electrode 5 is 2 mm~80 mm, or preferably 50 mm. The cation exchange membrane 6 is mounted inside the electrically insulative housing 8 in a parallel manner relative to and equally spaced between the positive electrode 7 and the negative electrode 5. Further, the positive electrode 7 can be a graphite plate, platinum plated metal, ruthenium iridium coated titanium plate, or titanium plate.

When using the continuous electrolyzed oxidizing/reduction water generator device, block the three water outlets 1;2;3 at first, and then fill water into the water inlet 4 to fill up the inside space of the continuous electrolyzed oxidizing/reduction water generator device, and then apply 5V~5000V, for example, 3000V DC across the positive electrode 7 and the negative electrode 5 for a predetermined length of time. Thereafter, open the three water outlets 1;2;3 to discharge water, keeping water intake ratio and the water output ratio in balance. Thus, electrolyzed oxidizing water is continuously provided.

Figure 4:
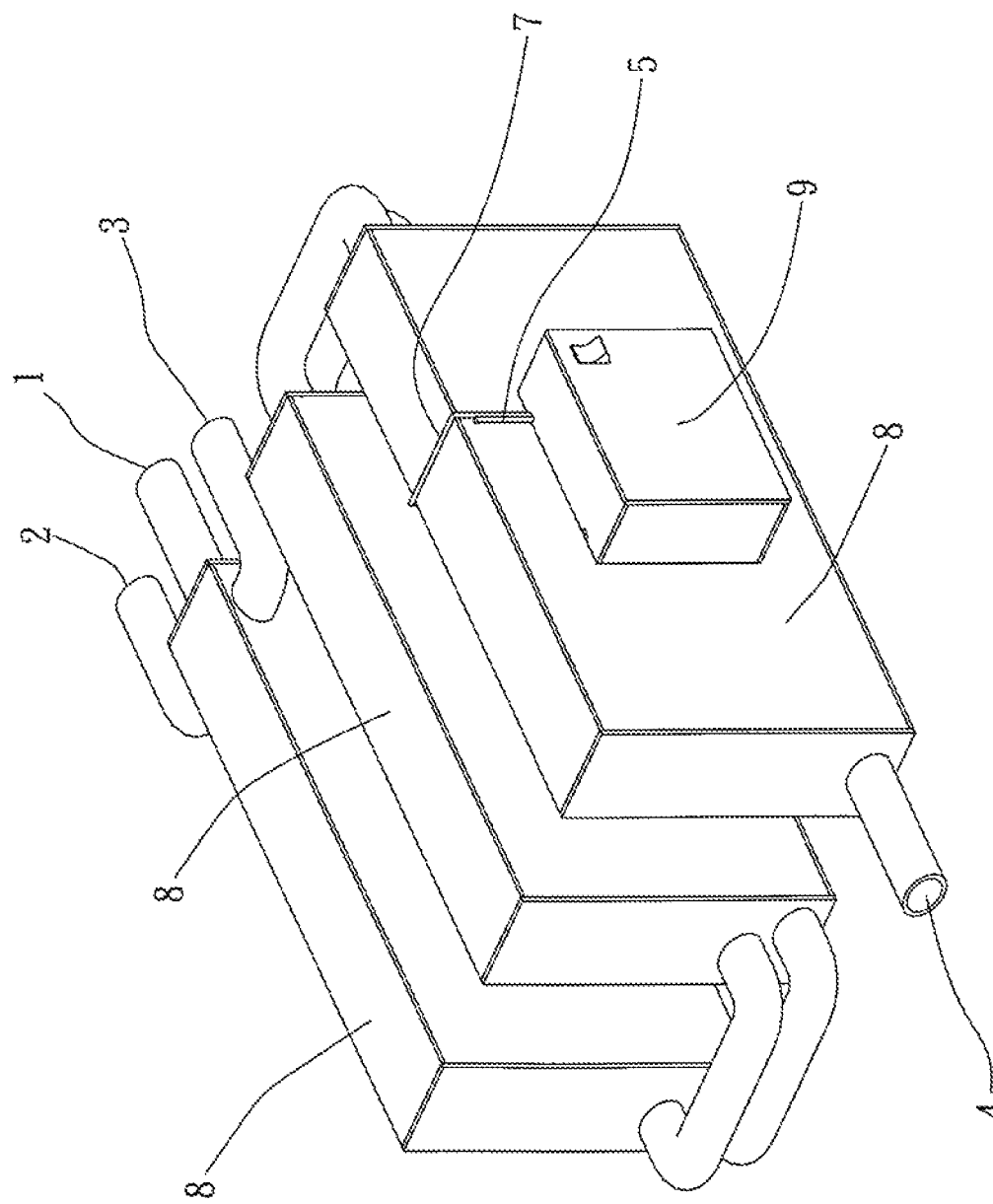
FIG. 4 is an oblique top elevational view of a continuous electrolyzed oxidizing/reduction water generator device in accordance with a second embodiment of the present invention.

FIG. 4 illustrates a continuous electrolyzed oxidizing/reduction water generator device in accordance with a second embodiment of the present invention. According to this second embodiment, the continuous electrolyzed oxidizing/reduction water generator device is a combination design, comprising a plurality of generator units connected in series and respectively configured substantially similar to the aforesaid first embodiment. Further, the positive electrodes 7 and negative electrodes 5 of the multiple generator units are electrically connected to the electric control box 9. Further, the water inlet 4 is located on the first generator unit for guiding in water, and the three water outlets 1;2;3 are located on the last (third) generator unit for guiding out electrolyzed oxidizing water.

Figure 5:
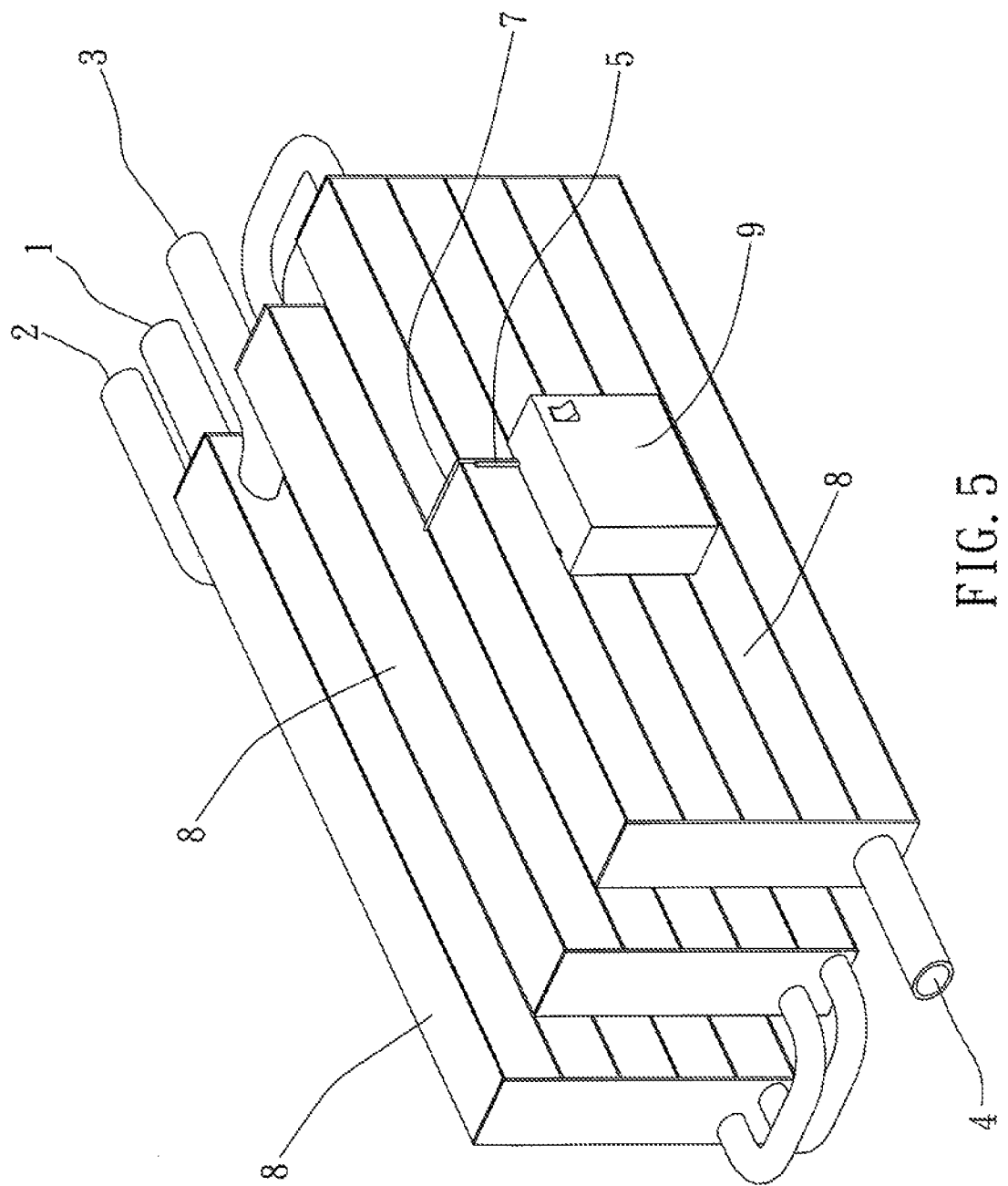
FIG. 5 is an oblique top elevational view of a continuous electrolyzed oxidizing/reduction water generator device in accordance with a third embodiment of the present invention.
Figure 6:
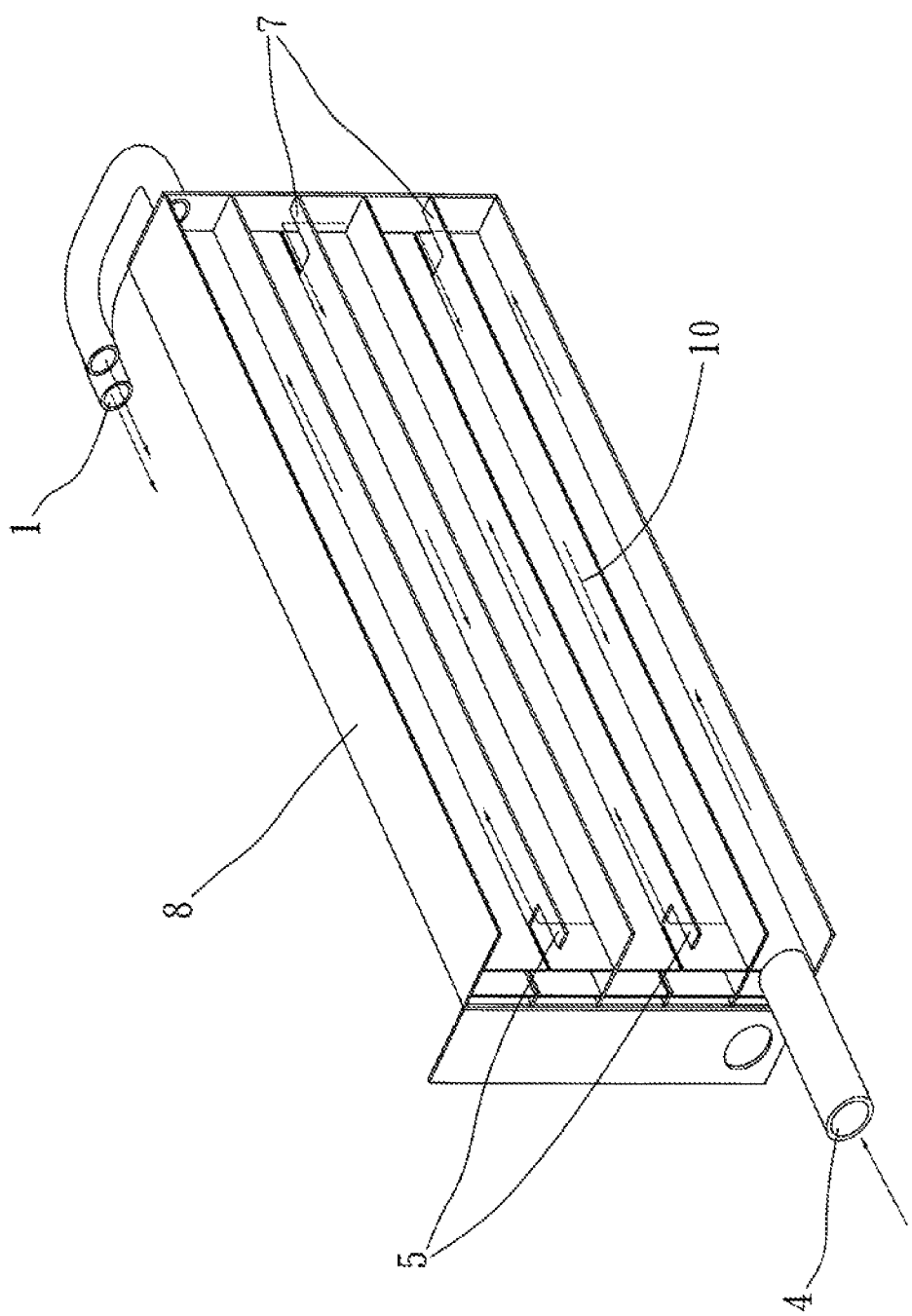
FIG. 6 is an opened view of a part of the continuous electrolyzed oxidizing/reduction water generator device in accordance with the third embodiment of the present invention, illustrating the internal structure of each individual generator unit.

FIGS. 5 and 6 illustrate a continuous electrolyzed oxidizing/reduction water generator device in accordance with a third embodiment of the present invention. This third embodiment is substantially similar to the aforesaid second embodiment with the exception that the electrically insulative housing 8 of each of the multiple generator units is divided into multiple electrically insulated chambers at different elevations; one positive electrode 7 and one negative electrode 5 are arranged in each of the multiple electrically insulated chambers in such a manner that a detoured water passageway 10 is defined in each generator unit, as shown in FIG. 6. According to this third embodiment, each of the multiple generator units eliminates the aforesaid cation exchange membrane 6.

A prototype of continuous electrolyzed oxidizing/reduction water generator device has been constructed with the features of FIGS. 1-6. The continuous electrolyzed oxidizing/reduction water generator device works smoothly to provide all of the features disclosed earlier.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A continuous electrolyzed oxidizing/reduction water generator device, comprising:
    a positive electrode, a negative electrode, a cation exchange membrane, an electrically insulative housing including a displaceably sealable panel, and an electric control box adapted to provide a high voltage DC across said positive electrode and said negative electrode;
    a water inlet located on one side of said electrically insulative housing; and
    at least one water outlet located on an opposite side of said electrically insulative housing, wherein said electrically insulative housing is an acid, alkali and pressure resistant box member having a rectangular cross section;
    said positive electrode and said negative electrode are longitudinally mounted inside said electrically insulative housing in a parallel manner and equally spaced between two opposite sidewalls of said electrically insulative housing and electrically connected to said electric control box;
    said cation exchange membrane is mounted inside said electrically insulative housing between said positive electrode and said negative electrode to define a first compartment and a second compartment, respectively, said at least one water outlet fluidly-communicated with both said first compartment and said second compartment for outputting water contained therein.

2. The continuous electrolyzed oxidizing/reduction water generator device as claimed in claim 1, wherein the distance between said positive electrode and said negative electrode is within 2 mm~80 mm; said cation exchange membrane is mounted inside said electrically insulative housing in a parallel manner relative to and equally spaced between said positive electrode and said negative electrode.

3. The continuous electrolyzed oxidizing/reduction water generator device as claimed in claim 1, wherein said electric control box is adapted to provide 5V~5000V DC across said positive electrode and said negative electrode.

4. The continuous electrolyzed oxidizing/reduction water generator device as claimed in claim 1, wherein said positive electrode is capable of oxidizing intake water into electrolyzed oxidizing water having a potential level between 800 mV~1500 mV and an acidic pH value when electrically conducted; said negative electrode is capable of oxidizing intake water into electrolyzed reduction water having a potential level between −800 mV~−1200 mV and an alkaline pH value when electrically conducted.

5. A continuous electrolyzed oxidizing/reduction water generator device, comprising:
    a plurality of generator units connected in series for allowing an intake flow of water to pass therethrough, each said generator unit comprising an electrically insulative housing, a positive electrode and a negative electrode mounted inside said electrically insulative housing in a parallel manner;
    an electric control box electrically connected with the positive electrodes and negative electrodes of said generator units and adapted to provide a high voltage DC across the positive electrodes and negative electrodes of said generator units;
    a water inlet located on one on end of the series of said generator units; and
    at least one water outlet located on an opposite end of the series of said generator units;
    wherein each said generator unit further comprises a cation exchange membrane mounted inside the electrically insulative housing thereof in a parallel manner relative to and equally spaced between the associating positive electrode and negative electrode to define a first compartment and a second compartment, respectively, said at least one water outlet fluidly-communicated with both said first compartment and said second compartment for outputting water contained therein.

6. The continuous electrolyzed oxidizing/reduction water generator device as claimed in claim 5, wherein said positive electrode is selected from the material group of graphite plate, platinum plated metal, ruthenium iridium coated titanium plate and titanium plate.

* * * * *